United States Patent [19]

Ohki et al.

[11] Patent Number: 5,166,327
[45] Date of Patent: Nov. 24, 1992

[54] PROCESS FOR PRODUCING 3'-DEOXY-3-'-FLUOROTHYMIDINE

[75] Inventors: Junji Ohki; Kazuo Itoh; Nobuhiro Mizutani, all of Tokyo; Shigeki Higuchi, Omiya; Junko Tanaka, Tokyo, all of Japan

[73] Assignee: Yuki Gosei Kogyo Co., Ltd., Tokyo, Japan

[21] Appl. No.: 736,928

[22] Filed: Jul. 29, 1991

[30] Foreign Application Priority Data

Jul. 31, 1990 [JP] Japan ................. 2-203729
Jan. 24, 1991 [JP] Japan ................. 3-23988

[51] Int. Cl.$^5$ ........................... C07D 239/56
[52] U.S. Cl. .......................... 536/23; 435/85; 435/87
[58] Field of Search ............ 536/23; 435/85, 87

[56] References Cited

U.S. PATENT DOCUMENTS

| | | |
|---|---|---|
| 4,882,316 | 11/1989 | Lambert et al. ............ 536/23 |
| 4,904,770 | 2/1990 | Starrett, Jr. et al. ......... 536/23 |
| 4,921,950 | 5/1990 | Wilson ..................... 536/23 |
| 4,954,485 | 9/1990 | Yoshioka et al. ........... 536/23 |
| 5,026,688 | 6/1991 | Agrawal ................... 536/23 |

FOREIGN PATENT DOCUMENTS

| | | |
|---|---|---|
| 323441 | 7/1989 | European Pat. Off. ........ 536/23 |
| 418007 | 3/1991 | European Pat. Off. ........ 594/314 |
| 48-10472 | 2/1973 | Japan . |
| 64-68325 | 3/1989 | Japan . |
| 10670 | 7/1991 | World Int. Prop. O. ...... 536/23 |

OTHER PUBLICATIONS

E. De Clerog et al., Tayets for the design of antiviral agents, pp. 203-230.
Pudlo et al, Tetrahedron Letters, vol. 31, No. 22, pp. 3101-3104 (1990).
"Zur Spaltung von 2,3'-Anhydronucleosiden mit Halogen-wasserstoffsauren", Zeitschrift für Chemie, vol. 23, 335 (1983).
V. G. Kowollik et al., "Ein neuer Zugang zu 1-(2-,3-Didesoxy-3-fluor-β-D-ribofuranosyl)-pyrimidinen", Journal für Praktische Chemie, vol. 315, 895 (1973).
V. G. Kowollik et al., "Cleavage of a 2,3'-Anhydro Ring by Hydrogen Fluoride", Nucleic Acid Chemistry, Part I, pp. 299-302 (1978).

Primary Examiner—Cecilia Tsang
Attorney, Agent, or Firm—Oliff & Berridge

[57] ABSTRACT

This invention provides a process for producing 3'-deoxy-'-fluorothymidine, which comprises allowing 3'-deoxy-'-fluoro-5'-mesylthymidine (the stating material) to react with an acetylating agent, selected from the group consisting of alkali metal salts of acetic acid, amine salts of acetic acid and ammonium acetate, in an aprotic, ploar solvent to form the 5'-acetyl derivative, and ammonium acetate, in an aprotic, polar solvent to form the 5'-acetyl derivative, and eliminating the 5'-acetyl group from this intermediate, thereby giving the objective 3'-deoxy-'-fluorotymidine.

According to the process of this invention described above, the 5'-mesyl derivative can be efficiently acetylated, and 3'-deoxy-'-fluorotymidine can be obtained in a high yield.

9 Claims, No Drawings

PROCESS FOR PRODUCING 3'-DEOXY-3-'-FLUOROTHYMIDINE

FIELD OF THE INVENTION

This invention relates to processes for producing 3'-deoxy-3'-fluorothymidine having antiviral and antitumor actions.

BACKGROUND OF THE INVENTION

It became known in recent years that nucleosides show a variety of physiological activities, and many natural and nonnatural nucleosides have been synthesized. Of these, 3'-deoxy-3'-fluorothymidine has drawn attention because of its activity against the virus causing AIDS, and the following four methods have been disclosed for the production of this compound.

(1) 3'-Mesylthymidine or 2,3'-anhydrothymidine is allowed to react with potassium hydrogen fluoride or ammonium fluoride in ethylene glycol at 191° C. for 10 to 90 minutes, thus giving 3'-deoxy-3'-fluorothymidine (yield: 10 to 14%) [Japanese Patent Publication No. 10472 (1973)].

(2) Reaction of thymidine with 4-chlorobenzoyl chloride in pyridine at 5° to 20° C. forms 5'-(4-chlorobenzoyl)thymidine (yield: 80%), which is then allowed to react with diethylaminosulfur trifluoride in methylene chloride at −78° C., thus giving 3'-deoxy-3'-fluorothymidine (yield: 19.9%) [Japanese Patent Kokai No. 68325 (1989)].

(3) Reaction of 2,3'-anhydro-5'-mesylthymidine with hydrogen fluoride in triethylamine at 150° C. for 90 minutes gives a mixture of 3'-deoxy-3'-fluorothymidine and 3'-deoxy-3'-fluoro-5'-mesylthymidine (yield: 19%) [Zeitschrift fur Chemie, 23, 335 (1983)].

(4) Reaction of 2,3'-anhydro-5'-mesylthymidine with hydrogen fluoride and aluminum fluoride in dioxane at 170° C. forms 3'-deoxy-3'-fluoro-5'-mesylthymidine (yield: 61%), which is then demesylated by the use of sodium hydroxide, thus giving 3'-deoxy-3'-fluorothymidine (yield: 46%) [Journal für Praktische Chemie, 315, 895 (1973)].

Any of these methods is not satisfactory as an industrial process, because the product yield is low, an expensive reagent has to be used, the reproducibility is low, or it is not easy to obtain the purified product.

Another synthetic method is also known, in which, after protecting the 5'-hydroxyl group in thymidine with mesyl group (an acid-resistant protective group), the 3'-position is fluorinated by the use of hydrogen fluoride to form 3'-deoxy-3'-fluoro-5'-mesylthymidine (hereinafter abbreviated as "5'-mesyl derivative"), followed by demesylation, thus giving 3'-deoxy-3'-fluorothymidine. The demesylation reaction, which is a step in this synthetic method, is generally carried out under alkaline conditions by the use of an alkali hydroxide, but this method is not applicable to the 5'-mesyl derivative because it contains a fluorine atom which is reactive with an alkali hydroxide. Hence, a method is used in this case, in which the mesyl group is first substituted with acetyl group by reaction with potassium acetate in acetic anhydride, and 5'-acetyl-3'-deoxy-3'-fluorothymidine thus formed (hereinafter abbreviated as "5'-acetyl derivative") is deacetylated, thus giving 3'-deoxy-3'-fluorothymidine [Nucleic Acid Chemistry, Part I, on pages 299–302 (1978)].

This acetylation reaction requires the use of acetic anhydride in an amount of about 100 times as much as that of the 5'-mesyl derivative and heating for a long time, entailing excessively colored reaction products, a large amount of by-products, and a very low yield of the 5'-acetyl derivative. Hence, column chromatography of low efficiency has to be used for purification, making it difficult to industrially produce the 5'-acetyl derivative in large quantities.

SUMMARY OF THE INVENTION

As a result of intensive studies to develop a highly efficient method of acetylating the 5'-mesyl derivative, the present inventors noticed that the acetylation proceeds smoothly in a solvent which dissolves the 5'-mesyl derivative and an acetylating agent selected from the group consisting of alkali metal salts of acetic acid, amine salts of acetic acid and ammonium acetate, and discovered the acetylation conditions of this invention which obviate the need for the use of acetic anhydride.

Thus, this invention provides a process for producing 3'-deoxy-3'-fluorothymidine represented by the formula shown below, which comprises allowing 3'-deoxy-3'-fluoro-5'-mesylthymidine (the starting material) to react with an acetylating agent, selected from the group consisting of alkali metal salts of acetic acid, amine salts of acetic acid and ammonium acetate, in an aprotic, polar solvent to form the 5'-acetyl derivative, and eliminating the 5'-acetyl group from this intermediate, thereby giving the objective 3'-deoxy-3'-fluorothymidine.

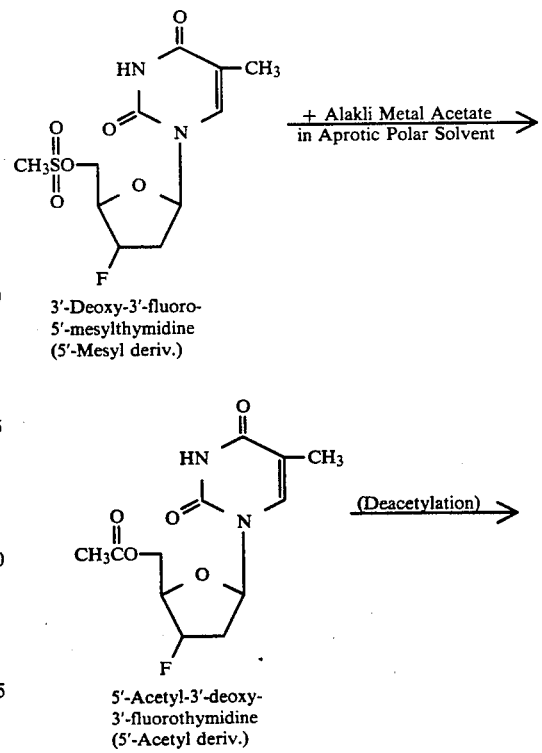

3'-Deoxy-3'-fluoro-5'-mesylthymidine
(5'-Mesyl deriv.)

5'-Acetyl-3'-deoxy-3'-fluorothymidine
(5'-Acetyl deriv.)

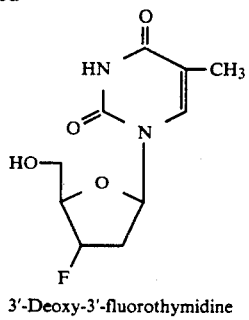

3'-Deoxy-3'-fluorothymidine

According to the process of this invention described above, the 5'-mesyl derivative can be efficiently acetylated, and 3'-deoxy-3'-fluorothymidine can be obtained in a high yield.

Thus, the process of this invention ensures stable supply of 3'-deoxy-3'-fluorothymidine—a useful compound having antiviral and antitumor activities and exhibiting a higher activity against AIDS than 3'-deoxy-3'-azidethymidine (AZT)—in large quantities, in a high yield and by simple operations, and is therefore a satisfactory industrial process.

DETAILED DESCRIPTION OF THE INVENTION

The 5'-mesyl derivative, which is the starting material in the process of this invention, can be obtained by reaction of thymidine with mesyl chloride in pyridine to form 3',5'-dimesylthymidine, and by reaction of this intermediate with sodium hydroxide in ethanol to form 2,3'-anhydro-5'-mesylthymidine, followed by reaction with aluminium fluoride in dioxane containing 0.1% hydrogen fluoride at an elevated temperature, as described on page 299 in Nucleic Acid Chemistry, Part I (1978).

The acetylating agents that may be used in this invention are alkali metal acetates (e.g., lithium, sodium and potassium acetates), amine salts of acetic acid (e.g., tetramethylammonium, tetraethylammonium, tetrapropylammonium and tetrabutylammonium acetates), and ammonium acetate.

An aprotic, polar solvent is used for the acetylation reaction; as its typical examples, there may be mentioned, among others, N,N-dimethylformamide, N,N-dimethylacetamide, dimethyl sulfoxide, hexamethylphosphoric triamide, N-methyl pyrrolidone, acetonitrile and acetone.

Acetylation of the 5'-mesyl derivative in the process of this invention requires the use of an acetylating agent in an amount at least equimolar to that of 3'-deoxy-3'-fluoro-5'-mesylthymidine, preferably in an amount of 1.4 to 3 mole proportions. Use of an acetylating agent in an excessive amount should be avoided because the reaction system becomes acidic.

The aprotic, polar solvent may be used in such an amount that dissolves the 5'-mesyl derivative; the reaction proceeds even when part of the acetylating agent is suspended in the solvent, but it is generally preferable to use the solvent in an amount equal to or more than that of the 5'-mesyl derivative on weight basis.

The reaction temperature should be 50° C. or higher and below the boiling point of the solvent used. The rate of acetylation will be very low if the temperature is below 50° C., and the reaction products are liable to coloration when the reaction temperature is close to the solvent's boiling point. Hence, the most preferable temperature range is from 80° to 130° C.

The reaction time may vary depending on the reaction temperature adopted and the types of reaction solvent and acetylating agent used, and is generally in the range from 10 to 120 minutes when the reaction is carried out at 110° C.

At the end of reaction, the reaction mixture may be used directly or as a concentrate to be obtained by removing the reaction solvent from the reaction mixture under the reduced pressure, for the succeeding deacetylation step. Alternatively, the 5'-acetyl derivative is extracted from the reaction mixture, or from a concentrate thereof, by using an organic solvent, the solvent is distilled off from the extract, and the concentrate thus obtained is used (after being purified, for example, by decolorization with activated charcoal, as required) for the deacetylation reaction.

The 5'-acetyl derivative thus obtained is then subjected to deacetylation by a known method, for example, by admixing ammonia-saturated methanol and allowing the resulting mixture to stand at a temperature in the range from 0° C. to room temperature with or without agitation [as described on page 299 in Nucleic Acid Chemistry, Part I (1978)].

The reaction mixture is decolorized by the use of activated charcoal, and the greyish-white, crude crystals of 3'-deoxy-3'-fluorothymidine thus obtained are purified, for example, by recrystallization from water, a lower alcohol or ethyl acetate; alternatively, the solvent is distilled off from the reaction mixture under reduced pressure, the remaining oil is treated with a synthetic adsorbant, the adsorbed 3'-deoxy-3'-fluorothymidine is eluted with an aqueous alcohol, the solvent is distilled off from the eluate, and the crude product thus obtained is purified, for example, by recrystallization from water or a lower alcohol, thereby giving 3'-deoxy-3'-fluorothymidine as white powder or white granular crystals of 99.8% or higher purity in a high yield of 70% or more.

EXAMPLES

The following examples will further illustrate the invention.

EXAMPLE 1

To a solution of 3.22 g (10 millimoles) of 3'-deoxy-3'-fluoro-5'-mesylthymidine in 10 ml dimethyl sulfoxide, was added 1.64 g (20 millimoles) of sodium acetate, and the mixture was heated at 110°±5° C. for ten minutes with stirring. Dimethyl sulfoxide was distilled off from the reaction mixture under reduced pressure, leaving about five grams of faint-brown oil. This oil showed the same retention time as a standard sample of 5'-acetyl-3'-deoxy-3'-fluorothynudube in high performance liquid chromatography and also showed the same $R_f$ value in thin-layer chromatography. Furthermore, in nuclear magnetic resonance spectrum, the peak of 3.25 ppm ($\delta$ value) corresponding to mesyl group had disappeared and the formation of 2.09 ppm peak corresponding to acetyl group was observed. Hence, it was confirmed that this oil is 5'-acetyl-3'-deoxy-3'-fluorothymidine.

To this faint-brown oil was added 60 ml of ammonia-saturated methanol, the mixture was stirred at room temperature for about two hours, and methanol was distilled off from the reaction mixture under reduced pressure, leaving faint brownish-red oil. Water (10 ml)

was added to this oil, the mixture was heated until a clear solution was obtained, and the solution was decolorized by treatment with activated charcoal. The charcoal was filtered off while hot and washed with 10 ml of hot water, the washings were admixed to the filtrate obtained above, and water was distilled off under reduced pressure from the combined solution. Water (10 ml) was added to the residue, the mixture was heated until a clear solution was obtained, and the solution was allowed to stand overnight at room temperature, thus giving 2.0 g (8.2 millimoles) of 3'-deoxy-3'-fluorothymidine as white, granular crystals. The yield was 82%.

Analytical Values (1) 3'-Deoxy-3'-fluoro-5'-mesylthymidine
Melting point: 165° ~ 166° C.
$^1$H-Nuclear magnetic resonance spectrum (DMSO-$d_6$): $\delta$(ppm)=1.77 (s, 3H, CH$_3$), 2.39 (m, 2H, H-2'×2), 3.25 (s, 3H, CH$_3$SO$_2$—), 4.38 (m, 1H, H-4'), 4.42 (m, 2H, H-5'×2), 5.37 (dd, J HH=4.0 Hz, J HF=52.2 Hz, 1H, H-3'), 6.24 (dd, J=8.6 Hz, J=6.0 Hz, 1H, H-1'), 7.51 (s, 1H, 6-H), 11.40 (brS, 1H, >NH).
$^{13}$C-Nuclear magnetic resonance spectrum (DMSO-$d_6$): $\delta$(ppm)=11.94 (CH$_3$), 36.08 (d, J=20.7 Hz, 2'-C), 36.76 (CH$_3$SO$_2$—), 68.83 (d, J=11.2 Hz, 5'-C), 81.39 (d, J=26.9 Hz, 4'-C), 84.45 (1'-C), 93.86 (d, J=176.6 Hz, 3'-C), 110.37 (5-C), 135.80 (6-C), 150.80 (2-C), 160.98 (4-C).

(2) 5'-Acetyl-3'-deoxy-3'-fluorothymidine
Melting point: 99° ~ 100° C.
$^1$H-Nuclear magnetic resonance spectrum (DMSO-$d_6$): $\delta$(ppm)=1.90 (d, J=1.22 Hz, 3H, CH$_3$), 2.09 (s, 3H, CH$_3$CO—), 2.23 (m, 1H, 2'-H), 2.62 (m, 1H, 2'-H), 4.36 (m, 2H, 5'-H), 4.37 (m, 1H, 4'-H), 5.18 (dd, J HH=5.3 Hz, J HF=51.6 Hz, 3'-H), 6.30 (dd, J=8.8 Hz, J=55 Hz, 1'-H), 7.22 (d, J=1.22 Hz, 6-H), 9.21 (brS, 1H, NH).
$^{13}$C-Nuclear magnetic resonance spectrum (DMSO-$d_6$): $\delta$(ppm)=12.43 (CH$_3$), 20.55 (CH$_3$CO—), 38.12 (d, J=21.3 Hz, 2'-C), 63.44 (d, J=10.2 Hz, 5'-C), 82.37 (d, J=26.7 Hz, 4'-C), 85.47 (1'-C), 93.44 (d, J=180.6 Hz, 3'-C), 111.57 (5-C), 134.83 (6-C), 150.41 (2-C), 163.82 (4-C), 170.32 (CH$_3$CO—).

(3) 3'-Deoxy-3'-fluorothymidine
Melting point: 177° ~ 179° C.
$^1$H-Nuclear magnetic resonance spectrum (DMSO-$d_6$): $\delta$(ppm)=1.77 (d, J=1.1 Hz, CH$_3$), 2.30 (m, 2H, H-2'×2), 3.64 (m, 2H, H-5'×2), 4.13 (td, J HH=4.0 Hz, J HF=27.8 Hz, 1H, H-4'), 5.29 (dd, J HH=4.0 Hz, J HF=54.2 Hz, 1H, H-3'), 6.20 (dd, J=5.9 Hz, J=9.1 Hz, 1-H, H-1'), 7.69 (d, J=1.1 Hz, 1H, H-6), 11.31 (brS, 1H, NH).
$^{13}$C-Nuclear magnetic resonance spectrum (DMSO-$d_6$): $\delta$(ppm)=12.16 (CH$_3$), 36.94 (d, J=20.3 Hz, 2'-C), 60.94 (d, J=11.1 Hz, 5'-C), 83.89 (1'-C), 84.94 (d, J=23.0 Hz, 4'-C), 95.03 (d, J=174.4 Hz, 3'-C), 110.00 (5-C), 136.04 (6-C), 150.82 (2-C), 164.03 (4-C).
Specific rotation [$\alpha$] (26°/D) −7.0° (c=1.0, DMSO).

EXAMPLE 2

To a solution of 3.22 g (10 millimoles) 3'-deoxy-3'-fluoro-5'-mesylthymidine in 10 ml N,N-dimethylformamide, was added 1.96 g (20 millimoles) potassium acetate, and the mixture was heated at 110°±5° C. for 60 minutes with stirring. The solvent was distilled off from the reaction mixture under reduced pressure, 30 ml water was added to the residue, and the mixture was extracted twice with 50 ml ethyl acetate. The extract was washed twice with 30 ml water and dried over anhydrous sodium sulfate, the solvent was distilled off from the dried extract under reduced pressure, and the residue was dissolved in methanol. This solution was decolorized by treatment with 1.4 g of activated charcoal, the decolorized solution obtained by filtering off the charcoal was concentrated, and the residue was treated with ammonia-saturated methanol and subjected to purification in the same way as in Example 1, giving 1.8 g (7.38 millimoles) of 3'-deoxy-3'-fluorothymidine as white, granular crystals. The yield was 73.8%.

The analytical values were the same as those of 3'-deoxy-3'-fluorothymidine obtained in Example 1.

EXAMPLE 3

To a solution of 644 g (2 moles) 3'-deoxy-3'-fluoro-5'-mesylthymidine in one liter of N,N-dimethylformamide, was added 308 g (4 moles) ammonium acetate, and the mixture was heated at 110°±5° C. for two hours with stirring. The solvent was distilled off from the reaction mixture under reduced pressure, leaving about 1 Kg of brown oil. This oil was confirmed to be 5'-acetyl-3'-deoxy-3'-fluorothymidine from the results of high performance liquid chromatography, thin-layer chromatography and nuclear magnetic resonance spectrum obtained in the same way as in Example 1.

To this oil was added six liters of ammonia-saturated methanol, the mixture was stirred at room temperature for about two hours, and methanol was distilled off from the reaction mixture under reduced pressure, leaving about 1 Kg of brown oil. This oil was dissolved in ten liters of water, the resulting solution was passed through ten liters of a synthetic adsorbent (Sepabeads/SP207 ®), the adsorbent was washed by passing 30 liters of water, and elution was performed by passing 30 liters of 50% aqueous methanol and 10 liters of methanol in that order. The eluate was concentrated under reduced pressure to dryness, leaving crude crystals of 3'-deoxy-3'-fluorothymidine (about 450 g) as white solid. Two liters of water was admixed to this white solid, the mixture was heated with stirring until a clear solution was obtained, and the solution was stirred at room temperature overnight, thus giving 410 g (1.68 moles) of 3'-deoxy-3'-fluorothymidine as white powdery crystals. The yield was 84%, and its analytical values were the same as those of 3'-deoxy-3'-fluorothymidine obtained in Example 1.

EXAMPLE 4

To a solution of 322 g (1 mole) 3'-deoxy-3'-fluoro-5'-mesylthymidine in 500 ml of dimethyl sulfoxide, was added 266 g (2 moles) tetramethylammonium acetate, and the mixture was heated at 110°±5° C. for 30 minutes with stirring. The solvent was distilled off from the reaction mixture under reduced pressure, leaving about 500 g of brown oil. This oil was confirmed to be 5'-acetyl-3'-deoxy-3'-fluorothymidine from the results of high performance liquid chromatography, thin-layer chromatography and nuclear magnetic resonance spectrum obtained in the same way as in Example 1.

To this oil was added three liters of ammonia-saturated methanol, the mixture was stirred at room temperature for about two hours, and methanol was distilled off from the reaction mixture under reduced pressure, leaving about 500 g of brown oil. This oil was dissolved in five liters of water, the resulting solution was passed through five liters of a synthetic adsorbent (Diaion HP20 ®), the adsorbent was treated in the same way as in Example 3, giving 195 g (0.80 mole) of 3'-deoxy-3'-fluorothymidine as white powdery crystals. The yield was 80%, and its analytical values were the same as those of 3'-deoxy-3'-fluorothymidine obtained in Example 1.

COMPARATIVE EXAMPLE

To a solution of 0.5 g (1.6 millimoles) 3'-deoxy-3'-fluoro-5'-mesylthymidine in 60 ml of acetic anhydride, was added 0.5 g (5.1 millimoles) potassium acetate, and the mixture was heated at 130° to 135° C. for two hours with stirring. The solvent was distilled off from the reaction mixture under reduced pressure, the dark brown residue thus obtained was dissolved in 125 ml chloroform, the resulting solution was washed with 100 ml water, decolorized with 0.1 g of activated charcoal and dried over anhydrous magnesium sulfate, and the solvent was distilled off from the dried solution, leaving 0.73 g of reddish-brown oil. Analysis of this oil by high performance liquid chromatography showed 27 peaks, in which the content of 5'-acetyl-3'-deoxy-3'-fluorothymidine was 20% (areal ratio).

What is claimed is:

1. A process for producing 3'-deoxy-3'-fluorothymidine, which comprises (1) the step of allowing 3'-deoxy-3'-fluoro-5'-mesylthymidine to react with an acetylating agent, selected from the group consisting of alkali metal salts of acetic acid, amine salts of acetic acid and ammonium acetate, in an aprotic, polar solvent to form 5'-acetyl-3'-deoxy-3'-fluorothymidine, and (2) the step of deacetylating 5'-acetyl-3'-deoxy-3'-fluorothymidine thus obtained, thereby giving 3'-deoxy-3'-fluorothymidine.

2. The process for producing 3'-deoxy-3'-fluorothymidine as defined in claim 1, wherein said acetylating agent is selected from lithium acetate, sodium acetate, potassium acetate, ammonium acetate, tetramethylammonium acetate, tetraethylammonium acetate, tetrapropylammonium acetate and tetrabutylammonium acetate.

3. The process for producing 3'-deoxy-3'-fluorothymidine as defined in claim 1 or 2, wherein said acetylating agent is used in an amount at least equimolar to that of 3'-deoxy-3'-fluoro-5'-mesylthymidine.

4. The process for producing 3'-deoxy-3'-fluorothymidine as defined in claim 1, wherein said aprotic, polar solvent is selected from N,N-dimethylformamide, N,N-dimethylacetamide, dimethyl sulfoxide, hexamethylphosphoric triamide, N-methyl pyrrolidone, acetonitrile and acetone.

5. The process for producing 3'-deoxy-3'-fluorothymidine as defined in claim 1 or 4, wherein said aprotic, polar solvent is used at least in an amount that dissolves 3'-deoxy-3'-fluoro-5'-mesylthymidine.

6. The process for producing 3'-deoxy-3'-fluorothymidine as defined in claim 1, wherein said acetylating agent is selected from sodium acetate, potassium acetate, ammonium acetate and tetramethylammonium acetate, and said aprotic, polar solvent is selected from N,N-dimethylformamide and dimethyl sulfoxide.

7. The process for producing 3'-deoxy-3'-fluorothymidine as defined in claim 1, wherein the reaction of 3'-deoxy-3'-fluoro-5'-mesylthymidine with said acetylating agent is carried out at a temperature of 50° C. or higher and below the boiling point of the solvent.

8. The process for producing 3'-deoxy-3'-fluorothymidine as defined in claim 3, wherein the molar ratio of acetylating agent to 3'-deoxy-3'-fluoro-5'-mesylthymidine ranges from about 1.4 to about 3.

9. The process for producing 3'-deoxy-3'-fluorothymidine as defined in claim 7, wherein the temperature ranges from about 80° C. to about 130° C.

* * * * *